United States Patent [19]
Ishida et al.

[11] Patent Number: 5,891,846
[45] Date of Patent: Apr. 6, 1999

[54] CYCLOSPORIN-CONTAINING EMULSION COMPOSITION

[75] Inventors: Masami Ishida; Takashi Suzuki, both of Yokohama, Japan

[73] Assignee: Shiseido Company, Ltd., Tokyo, Japan

[21] Appl. No.: 26,452

[22] Filed: Feb. 19, 1998

Related U.S. Application Data

[63] Continuation of Ser. No. 549,835, filed as PCT/JP95/00235, Feb. 17, 1995, abandoned.

[30]     Foreign Application Priority Data

Feb. 17, 1994    [JP]    Japan ..................................... 6-56533

[51] Int. Cl.$^6$ ................................................. A61K 38/13
[52] U.S. Cl. ........................... 514/11; 514/533; 514/547; 514/627; 514/871; 514/885; 514/938; 252/312
[58] Field of Search ............................. 514/11, 533, 547, 514/544, 627, 871, 885, 938; 252/312

[56]               References Cited

U.S. PATENT DOCUMENTS 5,504,068   4/1996   Komiya et al. .......................... 514/11

FOREIGN PATENT DOCUMENTS 2255623   10/1990   Japan .
5186365   7/1993   Japan .
5310591   11/1993   Japan .

OTHER PUBLICATIONS

Neal et al., "In Vitro Anti–Leishmanial Activity of compounds in Current Clinical Use for Unrelated Diseases", Drugs Exp. Clin. Res. (1988), 14(10), 621–628, 1988 month unavailable.

The Merck Index an Encyclopedia of Chemical, Drugs, and Biologicals, Tenth Edition, (merck & Co., Inc., Rahway, NJ, USA, 1983) p. 372, 1983 month unavilable.

Sakaki, et al., "Mechanisms of Augmented resistance of Cyclosporin A treated Mice to Influenza Virus Infection by Trehalose–6,6'–dimycolate", Microbiol. Immunol., 36(10) pp. 1061–1075, (1992) month unavailable.

The 19th Congress, International Federation of Societies of Cosmetic Chemists, pp. 71–133, (Jun. 7, 1976), Boston, Massachusetts.

Primary Examiner—Richard D. Lovering
Assistant Examiner—Daniel S. Metzmaier
Attorney, Agent, or Firm—Sprung Kramer Schaefer & Briscoe

[57]               ABSTRACT

A stable emulsion composition containing cyclosporin, a polyalkyl ester of polycarboxylic acid in the form of liquid at ordinary temperature, an oil component having an I.O.B. of 0 to 0.25 in the form of a liquid at ordinary temperature, and a surfactant.

7 Claims, 3 Drawing Sheets

CYCLOSPORIN-CONTAINING EMULSION COMPOSITION

This is a continuation of U.S. Ser. No. 08/549,835, filed Oct. 16, 1995, now abandoned which was filed under 35 U.S.C. 371 based on PCT/JP95/00235, filed Feb. 17, 1995.

TECHNICAL FIELD

The present invention relates to a novel cyclosporin-containing emulsion composition capable of containing cyclosporin in a high concentration, and having a superior stability and transdermal absorption, and no skin irritation. Cyclosporin is a cyclic peptide composed of 11 amino acids. Up until now, numerous types of natural or synthetic so-called "cyclosporin" called A-I etc. have been known. The "cyclosporin" referred to in the present invention includes these individual peptides and mixtures of these peptides.

BACKGROUND ART

Cyclosporin has been used as an immunosuppressant or antiinflammatory agent in organ transplants, for example, heart, lung, liver, kidney, pancreas, skin, cornea, and numerous other heterotransplants. In addition, it has been widely used for autoimmune diseases, for example, psoriasis gravis, Behcet's syndrome, Graves' disease, posterior uvetis, Crohn's disease, diabetes mellitus, ulcerative colitis, myasthenia gravis, rheumatoid arthritis, etc. Its efficacy in these has been reported.

In particular, efficacy by oral administration has been confirmed up to now for psoriasis. Many clinical test results have been reported at present (for example, British Journal of Dermatology, vol. 122, suppl. 36, 1990). In the case of oral administration, however, many side effects such so kidney toxicity, liver toxicity, specific to cyclosporin have been reported. Further, the bioavailability when orally administed is as low as about 30% and an amount of administration is difficult to determine due to the individual differences. Thus, there are many problems in treatment by oral administration.

In view of the above situations, methods of treatment involving direct application to the diseased part the psoriasis for transdermal absorption have been tried out and the development of an effective external agent free from the above side effects is desired. However, since cyclosporin is an active agent characterized by a large molecular weight and a high hydrophobicity, transdermal absorption of cyclosporin cannot be expected in the case of some preparations in which cyclosporin is dispersed in lyophilic bases such as white petrolatum and liquid paraffin or hydrophilic base such as polyethylene glycols.

Further, since cyclosporin dissolves well in methanol, ethanol, acetone, ether, chloroform, etc., external administration by a preparation in which cyclosporin is dissolved in an alcohol, particularly ethanol, has been considered. However, since crystals of cyclosporin easily precipitate after the alcohol evaporates, it is not possible to include the active ingredient at a high concentration and therefore it is not possible to ensure a sufficient amount for treatment be absorbed through the skin. Further, in the case of psoriasis or atopic dermatitis requiring long term continuous use, an alcohol-containing preparation cannot necessarily be said to be preferable when considering skin safety.

As prior art relating to cyclosporin-containing compositions, emulsion preparations containing medium chain fatty acid diglycerides or monoglycerides are disclosed in Japanese Unexamined Patent Publication (Kokai) No. 2-49733, emulsion compositions containing hydrophilic components, medium chain fatty acid triglycerides, and surfactants are disclosed in Japanese Unexamined Patent Publication (Kokai) No. 2-121929, pharmaceutical compositions composed of fatty acid saccharide monoesters and diluents are disclosed in Japanese Unexamined Patent Publication (Kokai) No. 2-235817, pharmaceutical compositions composed of fatty acid triglycerides, partical fatty acid glycerides, etc. are disclosed in Japanese Unexamined Patent Publication (Kokai) No. 2-255623, and emulsion compositions containing medium chain fatty acid triglycerides, vegetable oils, surfactants, etc. are disclosed in Japanese Unexamined Patent Publication (Kokai) No. 2-290809.

However, even with these prior arts, since it was impossible to formulate the cyclosporin at a high concentration and, also since, the stability of the preparations was insufficient, these have not been yet commercialized.

DISCLOSURE OF INVENTION

Accordingly, the object of the present invention is to provide an emulsion composition having superior stability and excellent transdermal absorption as an external agent even when a high concentration of cyclosporin is formulated.

In accordance with the present invention, there is provided a cyclosporin-containing oil-in-water type emulsion composition comprising (a) cyclosporin, (b) a polycarboxylate polyalkyl ester in the form of a liquid at ordinary temperature, (c) an oil component having an I.O.B. of 0 to 0.25 in the form of a liquid at ordinary temperature, and (d) a surfactant.

BRIEF DESCRIPTION OF THE DRAWINGS

The present invention will be further explained in detail below with reference to the drawings.

BEST MODE FOR CARRYING OUT THE INVENTION

The present invention will now be explained in detail.

The present inventors found that, when a polyalkyl ester of polycarboxylic acid for a lyophilic component is used, it is possible to formulate cyclosporin at a high concentration and further possible to obtain a cyclosporin emulsion composition which is stable as a preparation.

The amount of the cyclosporin formulated in the present invention is preferably 0.1 to 10% by weight, more preferably 0.5 to 5% by weight, based on the weight of the emulsion composition.

The polyalkyl ester of polycarboxylic acid formulated in the present invention may be those which are liquid at ordinary temperature. The esters having a total carbon atom number of 10 to 25 are preferable and the esters of a polycarboxylic acids having at least two carboxyl groups and linear or branched alcohols, in which the carboxyl group may be an aliphatic group, aromatic aliphatic group, or aromatic group having the carboxyl groups bonded aliphatically or aromatically are preferable. In the present invention, a partial ester compound may also be used. These esters may be used alone or in the mixture of two kinds or more. The content is not particularly limited as far as the cyclosporin can be dissolved. 2 to 50% by weight, more preferably 5 to 40% by weight, particularly preferably 5 to 30% by weight, based on the weight of the emulsion composition.

Specific examples of the polyalkyl ester polycarboxylic acid include, adipic dialkyl esters of a total of 12 to 22 carbon atoms, pimelic dialkyl esters having a total of 13 to 23 carbon atoms, dialkyl suberate azelaic dialkyl esters having a total of 13 to 21 carbon atoms, sebacic dialkyl esters having a total of 14 to 22 carbon atoms, phthalic dialkyl esters having a total of 14 to 24 carbon atoms (however, these alkyl groups may be straight or branched and the alkyl portion of the dialkyl may be the same or different), etc.

Preferable examples among these are dibutyl phthalate, diethyl phthalate, diisobutyl phthalate, dibutyl sebacate, diethyl sebacate, diisopropyl azelate, diisopropyl adipate, dibutyl adipate, and diisobutyl adipate.

The content of the cyclosporin is, as mentioned above, preferably 0.1 to 15% by weight. If the content is too small, the preparation is easily made, but there is a tendency for the pharmacological effect to become inferior, and therefore, this is not preferable. Conversely, if the content is too much, it is necessary to formulate a large amount of the polyalkyl ester of polycarboxylic acid for dissolving the cyclosporin and, as a result, the polarity may become high, and therefore the emulsion composition will become unstable. Note that if an oil component having an I.O.B. of 0 to 0.25 is added, a stable emulsion composition can be obtained even if a large amount of a polyalkyl ester of polycarboxylic acid is formulated.

As the oil component having an I.O.B. of 0 to 0.25, a triglyceride (e.g., olive oil, soybean oil, rapeseed oil, coconut oil, etc.), a synthetic ester oil (e.g., oleyl oleate, isopropyl myristate, cetyl myristate, etc.), or squalane, liquid paraffin, silicone oil, etc. may be used. Further, these oil components may be used alone or in any mixture thereof.

The oil component preferably has a molecular weight of at least about 200 and preferably is in the form of a liquid at ordinary temperature from the standpoint of handling. The content of the oil component is preferably 1/50 to an equal amount, more preferably 1/20 to 1/2, of the total weight of the cyclosporin and the polyalkyl ester polycarboxylic acid. When the content of the oil component is too small, it is not preferable from the standpoint of the stability of the emulsion composition, while conversely the content is too large, a content sometimes leads to precipitation of crystals of the cyclosporin.

According to the present invention, it is possible to formulate one or more types of oil components having an I.O.B. of more than 0.25 to but not more than 0.85 in the form of a liquid at ordinary temperature as a solution of the cyclosporin to the polyalkyl ester polycarboxylic acid. If a small amount of the oil component is added, it is possible to greatly reduce the amount of the polyalkyl ester polycarboxylic acid used and, further, to enable a large amount of cyclosporin to be dissolved, and therefore, is convenient.

As the oil component, specifically, crotamiton, benzyl alcohol, phenetyl alcohol, higher alcohol (e.g., 2-octyldodecanol, oleyl alcohol, 2-hexyldecanol, etc.), higher fatty acids (e.g., oleic acid, linolic acid, linoleic acid, etc.), etc. may be used. Particularly, crotamiton is preferred. The content of the oil component is preferably 0.1 to 10% by weight more preferably 0.5 to 5% by weight, based on the total weight of the cyclosporin and the polyalkyl ester polycarboxylic acid. The content of the polyalkyl ester of polycarboxylic acid in this case is 5 to 30% by weight.

Note that the I.O.B. (i.e., Inorganic Organic Balance) referred to in the present invention is the ratio of the inorganic and organic property calculated in accordance with the method of calculation of Fujita described in "Kagaku no Ryoeki", Vol. 11, No. 10, pp. 719 to 725 (1957), that is, the value given by the following formula:

$$\text{I.O.B.} = \Sigma(\text{inorganic property})/\Sigma(\text{organic property})$$

As the surfactant, any surfactants such as anionic surfactants (esters: sorbitan fatty acid ester, glycerol fatty acid ester, decaglycerol fatty acid ester, propylene glycol fatty acid ester, polyoxyethylene hydrogenated castor oil, etc., ethers: polyoxyethylene alkyl ether, polyoxyethylene polyoxypropylene alkyl ether, etc.), ionic surfactants (sodium lauryl sulfate, sodium cetyl sulfate, etc.), bipolar surfactants (betaine, aminocarboxylic acid, etc.) may be used. These may be used alone or in any mixture thereof. The content is preferably 0.5 to 15% by weight, more preferably 1 to 10% by weight, particularly preferably 1 to 7% by weight, based on the total weight of the emulsion composition. If the amount of the surfactant is too small, there is a danger of the emulsion composition becoming unstable, while if too large, there is a danger of the feeling at use becoming rough.

When the preparation is made a cream preparation, naturally, it is of course possible to add a solid higher fatty acid (e.g., palmitic acid, stearic acid, behenic acid, etc.) or higher alcohol (e.g., cetyl alcohol, stearyl alcohol, behenyl alcohol, etc.). Further, it is possible to add a semisolid oil component (e.g., vaseline, hydrogenated oil, etc.). Further, it is possible to thicken the preparation by adding a water soluble polymer to form the cream preparation. As the water soluble polymer in this case, for example, a carboxylvinyl polymer, sodium carboxylmethylcellulose, hydroxymethylcellulose, hydroxyethylcellulose, hydroxypropylcellulose, polyvinyl alcohol, polyvinyl pyrrolidone, etc. may be used.

These may be used alone or in any mixture thereof.

Further, a neutralizing agent for adjusting the pH of the preparation (e.g., inorganic bases such as sodium hydroxide, potassium hydroxide, and ammonia water and organic bases such as triethylamine, triethanolamine, and diisopropanolamine) may be used. If desired, it is also possible to add a humectant (e.g., propylene glycol, 1,3-butylene glycol, dipropylene glycol, glycerine, etc.), preservative (e.g., methyl p-hydroxylenzoate, ethyl paraven, propyl paraven, benzalkonium chloride, benzethonium chloride, etc.), antioxidant (e.g., dibutylhydroxytoluene, ascorbic acid, dl-α-tocopherol, sodium edetate, etc.)

When an emulsion or cream is formed, as one aspect of the present invention, water is an essential component. The water is included preferably in an amount of 20 to 90% by weight.

The cyclosporin-containing preparation according to the present invention may be produced in any process for producing emulsion compositions known to these skilled in the art. For example, it may be produced by adding cyclosporin to a polyalkyl ester of polycarboxylic acid, followed by heating the same to dissolve, then gradually adding an oil component while cooling to room temperature to obtain an oil phase. On the other hand, the aqueous phase is produced by adding a surfactant to a humectant, followed by heating the same to dissolve, then adding water thereafter, the oil phase is added to the aqueous phase under high speed stirring to effect the emulsification, whereby a cyclosporin-containing emulsion composition can be obtained.

In the present invention, a stable emulsion composition can be obtained regardless of the particle size of the emulsion, and therefore, the emulsification may be effected by an ordinary homomixer. However, it is also possible to produce the same by a high speed rotary type emulsifier such as an ultrasonic homogenizer (made by Ultrasonic Co. of the U.S.) or a Polytron emulsifier (Polytron® Type PT45/50 made by Kinematika of Switzerland). Further, to obtain an emulsion composition having a fine emulsion particle size, a pressurizing emulsifier such as a Manton-Gaulin homogenizer (Type 15M-8TA of Gaurin Co. of the U.S.) or a microfluidizer (Type 110T of Microfluidizer Co. of the U.S.) may be used.

EXAMPLES

The present invention will be explained in further detail, but is not of course limited to these Examples. Note that "percent" used herein, unless otherwise indicated, means "percent by weight".

Example 1

Formulation

| Component | % |
|---|---|
| (1) Cyclosporin | 1 |
| (2) Diisopropyl adipate | 5 |
| (3) Dibutyl sebacate | 5 |
| (4) Olive oil | 2 |
| (5) Liquid paraffin | 3 |
| (6) P. O. E. (20) sorbitan monostearate | 2.8 |
| (7) Monoglycerylstearate | 2 |
| (8) Glycerol | 10 |
| (9) Carboxyvinyl polymer | 0.2 |
| (10) Diisopropanolamine | q.s. |
| (11) Preservative | q.s. |
| (12) Purified water | Balance |
| Total | 100% |

Method of Preparation

The component (1) was added to the components (2) and (3). The mixture was then warmed to effect dissolution. To the resultant mixture was added the components (4) and (5) to prepare an oil phase. On the other hand, a part of the component (12) was added to the components (6), (7), and (8). The resultant mixture were then warmed to cause dissolution. To the resultant mixture was added the previously prepared oil phase. The resultant mixture was ultrasonically emulsified to prepare an emulsion. The components (9) and (11) were stirred and disssolved in the remaining part of the component (12). To the resultant mixture was added the component (10) to adjust the pH neutral. The resultant mixture was added to the previously prepared emulsion. The mixture stirred until homogeneous to prepare an emulsion preparation. The particle size of the emulsion of the preparation was 1 μm or less. No crystals of cyclosporin could be observed.

Example 2

Formulation

| Component | % |
|---|---|
| (1) Cyclosporin | 5 |
| (2) Crotamiton | 2 |
| (3) Diethyl sebacate | 15 |
| (4) Squalane | 4 |
| (5) P. O. E. (55) monOstearate | 2 |
| (6) Decaglycerine monooleate | 1 |
| (7) 1,3-Butyleneglycol | 8 |
| (8) Carboxylvinyl polymer | 0.8 |
| (9) Diisopropanolamine | q.s. |
| (10) Preservative | q.s. |
| (11) Purified water | Balance |
| | 100% |

Method of Preparation

The component (1) was added to the components (2) and (3). These components were then warmed to cause dissolution. To the resultant mixture was added the component (4) to prepare an oil phase. On the other hand, a part of the component (11) was added to the components (5), (6), and (7). These were then warmed to cause dissolution. To the resultant mixture was added the previously prepared oil phase. The mixture was emulsified using a homomixer to prepare an emulsion. The components (8) and (10) were warmed to dissolve in the remaining part of the component (11). To the resultant mixture was added the component (9) to adjust the pH neutral. The resultant mixture was added to the previously prepared emulsion. The mixture was stirred until homogeneous to prepare a cream preparation. The particle size of the emulsion of the preparation was 1 μm or less. No crystals of cyclosporin could be observed.

Example 3

Formulation

| Component | % |
|---|---|
| (1) Cyclosporin | 5 |
| (2) Crotamiton | 2 |
| (3) Diethyl sebacate | 15 |
| (4) Squalane | 4 |
| (5) P. O. E. (55) monstearate | 2 |
| (6) Decaglycerine monooleate | 1 |
| (7) 1,3-Butyleneglycol | 8 |
| (8) Stearyl alcohol | 1.5 |
| (9) Cetyl alcohol | 3.5 |
| (10) Stearic acid | 1.5 |
| (11) Panasate 875 | 1 |
| (12) p-hydroxylenzoate | q.s. |
| (13) Tenos MG | 3 |
| (14) Sodium cetyl sulfate | 0.2 |
| (15) Purified water | Balance |
| Total | 100% |

Method of Preparation

The component (1) was added to the components (2) and (3). These were then warmed to cause dissolution. To the resultant mixture was added the component (4) to prepare an oil phase. On the other hand, part of the component (15) was added to the components (5), (6), and 7. These were then warmed to dissolve. To the resultant mixture was added the previously prepared oil phase. The mixture was emulsified using a homomixer to prepare an emulsion (component A). The components (8), (9), (10), (11), (12), and (13) were warmed to dissolve and prepare an oil phase. The component (14) was dissolved in the remains by part of the component (15), then the previous oil phase was added. The mixture was emulsified by a homogenizer to prepare an emulsion (component B). The component (A) was added to the component (B). The mixture was stirred to mix then, then were cooled to obtain a cream preparation. The particle size of the emulsion of the preparation was less than 1 μm. No crystals of cyclosporin could be observed.

Example 4

Formulation

| Component | % |
|---|---|
| (1) Cyclosporin | 10 |
| (2) Diethyl sebacate | 30 |
| (3) Oleic acid | 5 |
| (4) Liquid paraffin | 7 |
| (5) P. O. E. (60) hydrogenated castor oil | 2 |
| (6) P. O. E. (25) cetyl ether | 1.5 |
| (7) Propylene glycol | 10 |
| (8) Carboxylvinyl polymer | 0.8 |
| (9) Potassium hydroxide | q.s. |
| (10) Preservative | q.s. |
| (11) Purified water | Balance |
| Total | 100% |

Method of Preparation

The component (1) was added to the component (2). These were then warmed to cause dissolution. To the resultant mixture was added the components (3) and (4) to prepare an oil phase. On the other hand, a part of the component (11) was added to the components (5), (6), and (7). These were then warmed to cause dissolution. To the resultant mixture was added the previously prepared oil phase. The resultant mixture was emulsified using a homomixer, then a Manton-Gaulin homogenizer was used to emulsify the resultant mixture under pressure to prepare an emulsion. Further, the component (8) was stirred and dissolved in the remaining part of the component (11). To the resultant mixture was added the component (9) to adjust the pH neutral. To the resultant mixture was added the previously prepared emulsion. The mixture was stirred until homogeneous to obtain a cream preparation. The particle size of the emulsion of the preparation was 1 μm or less. No crystals of cyclosporin could be observed.

Example 5

Formulation

| Component | % |
|---|---|
| (1) Cyclosporin | 5 |
| (2) Dibutyl phthalate | 20 |
| (3) Oleooleate | 5 |
| (4) Liquid paraffin | 5 |
| (5) P. O. E. (45) stearate | 5 |
| (6) Potassium stearate | 0.5 |
| (7) Propylene glycol | 8 |
| (8) Glycerol | 2 |

-continued

| Component | % |
|---|---|
| (9) Preservative | q.s |
| (10) Purified water | Balance |
| Total | 100% |

Method of Preparation

The component (1) was added to the component (2). These were then warmed to cause dissolution. To the resultant mixture was added the components (3) and (4) to prepare an oil phase. On the other hand, a part of the component (10) was added to the components (5), (6), (7), and (8). These were then warmed to cause dissolution. To the resultant mixture was added the previously prepared oil phase. These were emulsified by a homomixer. Further, a Manton-Gaulin homogenizer was used to emulsify the resultant mixture under pressure to prepare an emulsion. Further, the component (9) was stirred and dissolved in the remaining part of the component (10). To the resultant mixture was added the previously prepared emulsion. The mixture was stirred until homogeneous to obtain an emulsion. The particle size of the emulsion of the preparation was 1 μm or less. No crystals of cyclosporin could be observed.

Example 6

Formulation

| Component | % |
|---|---|
| (1) Cyclosporin | 3 |
| (2) Dibutyl adipate | 20 |
| (3) Isopropyl myristate | 2 |
| (4) Squalane | 3 |
| (5) Decaglycerine monooleate | 3 |
| (6) Hydrated lecithin | 0.5 |
| (7) 1,3-butyleneglycol | 3 |
| (8) Glycerol | 12 |
| (9) Preservative | q.s. |
| (10) Purified water | Balance |
| Total | 100% |

Method of Preparation

The component (1) was added to the component (2). These were then warmed to cause dissolution. To the resultant mixture was added the components (3) and (4) to prepare an oil phase. On the other hand, a part of the component (10) was added to the components (5), (6), (7), and (8). These were then warmed to cause dissolution. To the resultant mixture was added the previously prepared oil phase. These were emulsified using a Polytron emulsifier to prepare an emulsion. Further, the component (9) was stirred and dissolved in the remaining part of the component (10). To the resultant mixture was added the previously prepared emulsion. The mixture was stirred until homogeneous to obtain an emulsion. The particle size of the emulsion of the preparation was 1 μm or less. No crystals of cyclosporin could be observed.

Example 7

Formulation

| Component | % |
| --- | --- |
| (1) Cyclosporin | 5 |
| (2) Crotamiton | 2 |
| (3) Dibutyl phthalate | 8 |
| (4) Oleic acid | 2 |
| (5) Squalane | 9 |
| (6) Propylene glycol | 2 |
| (7) P. O. E. (55) monostearate | 1.5 |
| (8) Dodecyldimethylaminoxide | 1 |
| (9) Sodium cetyl sulfate | 0.2 |
| (10) Cetyl alcohol | 2.5 |
| (11) Stearyl alcohol | 4 |
| (12) Behenic acid | 1 |
| (13) White petrolatum | 8 |
| (14) Tenos MG | 3 |
| (15) Carboxylvinyl polymer | q.s. |
| (16) Glycerol | q.s. |
| (17) Sodium edetate | q.s. |
| (18) Sodium hydroxide | q.s. |
| (19) Preservative | q.s. |
| (20) Purified water | Balance |
| Total | 100% |

Method of Preparation

The component (1) was added to the components (2) and (3). These were then warmed to cause dissolution. The component (4) and a part of (5) were then added thereto to prepare an oil phase. On the other hand, a part of the component (20) was added to the components (6), (7), (8), and (9). These were then warmed to cause dissolution. To the resultant mixture was added the previously prepared oil phase. The resultant mixture was emulsified by a homomixer to prepare an emulsion (component A). The remaining part of the component (5) and the components (10), (11), (12), (13), and (14) were warmed to dissolve to prepare an oil phase. Further, the components (15), (16), (17), (18), and (19) were dissolved in the balance of the component (20), then the previous oil phase was added. The mixture was emulsified by a homogenizer to prepare an emulsion (component B). Further, the component A was added to the component B. They were stirred to mix them and then were cooled to obtain a cream preparation. The particle size of the emulsion of the preparation was 1 μm or less. No crystals of cyclosporin were observed.

Reference Example 1

Formulation

| Component | % |
| --- | --- |
| (1) Cyclosporin | 5 |
| (2) Ethyl alcohol | 10 |
| (3) Olive oil | 73 |
| (4) P. O. E. (5) glycerylmonostearate | 5 |
| (5) Aerosil 200 | 7 |
| Total | 100% |

Method of Preparation

The component (3) was added to the component (4). These were then warmed to cause dissolution, then the resultant mixture was cooled. To this was added a solution obtained by adding the component (2) to the component (1) to dissolve the same, then the component (5) was added. The mixture was stirred and mixed to obtain a gel preparation.

Experiment 1 (Stability Test)

Samples of about 5 g of the cream preparation of Example 2 were filled and sealed in 20 ml glass containers, which were then stored in constant temperature vessels of room temperature and 40° C. The changes in outer appearance, precipitation of crystals, and changes in content of the active component were examined. Note that as the control, the product of Reference Example 1 was used. The content was assayed using the liquid chromatography method. The results are shown in Table 1.

TABLE 1

| | Days (months) | | | |
| --- | --- | --- | --- | --- |
| | 1 | 2 | 4 | 6 |
| Outer appearance | No change | No change | No change | No change |
| Presence of crystals | None | None | None | None |
| Content (stored at room temperature) | 100.0% | 99.4% | 99.0% | 98.2% |
| Content (stored at 40° C.) | 99.4% | 98.9% | 98.5% | 98.0% |

As a result, it was found that the product of the present invention was free from precipitation of crystals over a long period and was superior in heat stability. On the other hand, the gel preparation of Reference Example 1 was observed to have immediate precipitation of crystals along with the evaporation of the alcohol.

Experiment 2 (In Vitro Permeation Test)

Figure 1:
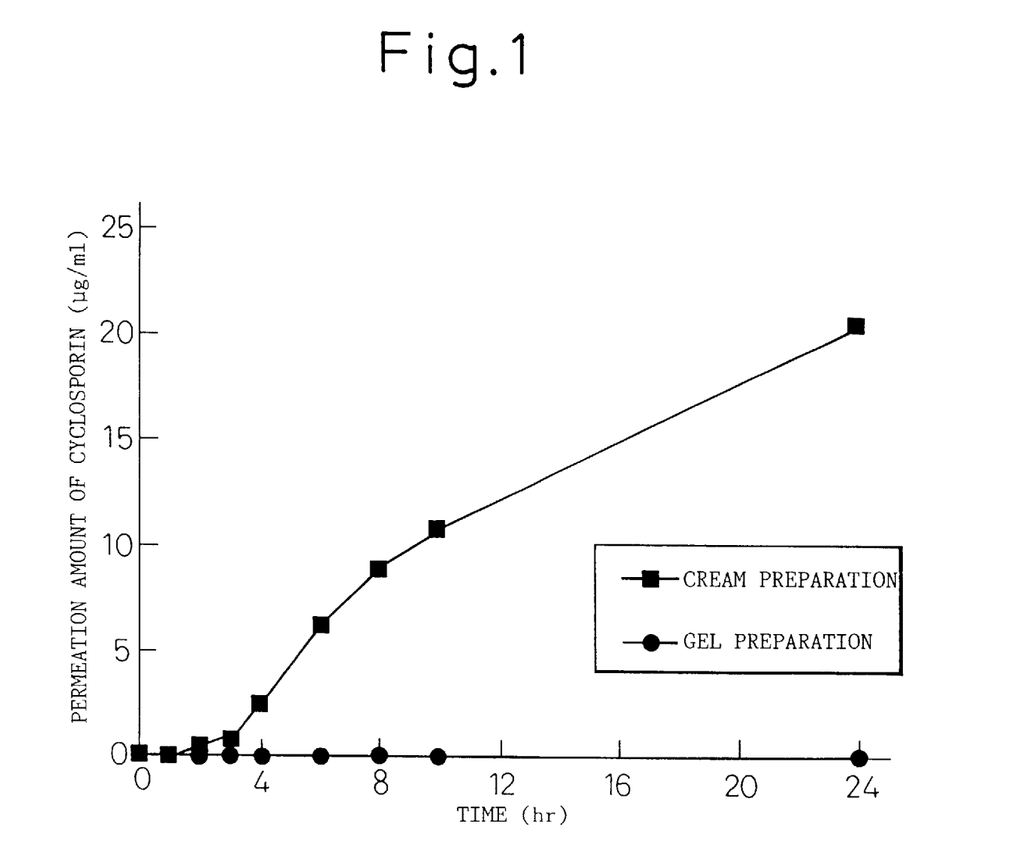
FIG. 1 is a graph showing drug permeation properties of the cream preparation of Example 2 and the gel preparation of Reference Example 1.

The skin permeation of cyclosporin was examined for the cream preparation of Example 2 and the gel preparation of Reference Example 1 using snake skin. For the apparatus, a longitudinal Franz cell was used. The assay was performed by the liquid chromatography method. The results are shown in FIG. 1.

From the results, it was observed that the skin permeation property of the product according to the present invention was superior to that of a conventional preparation dissolved in alcohol.

Experiment 3 (Transdermal Absorption Test)

Figure 2:
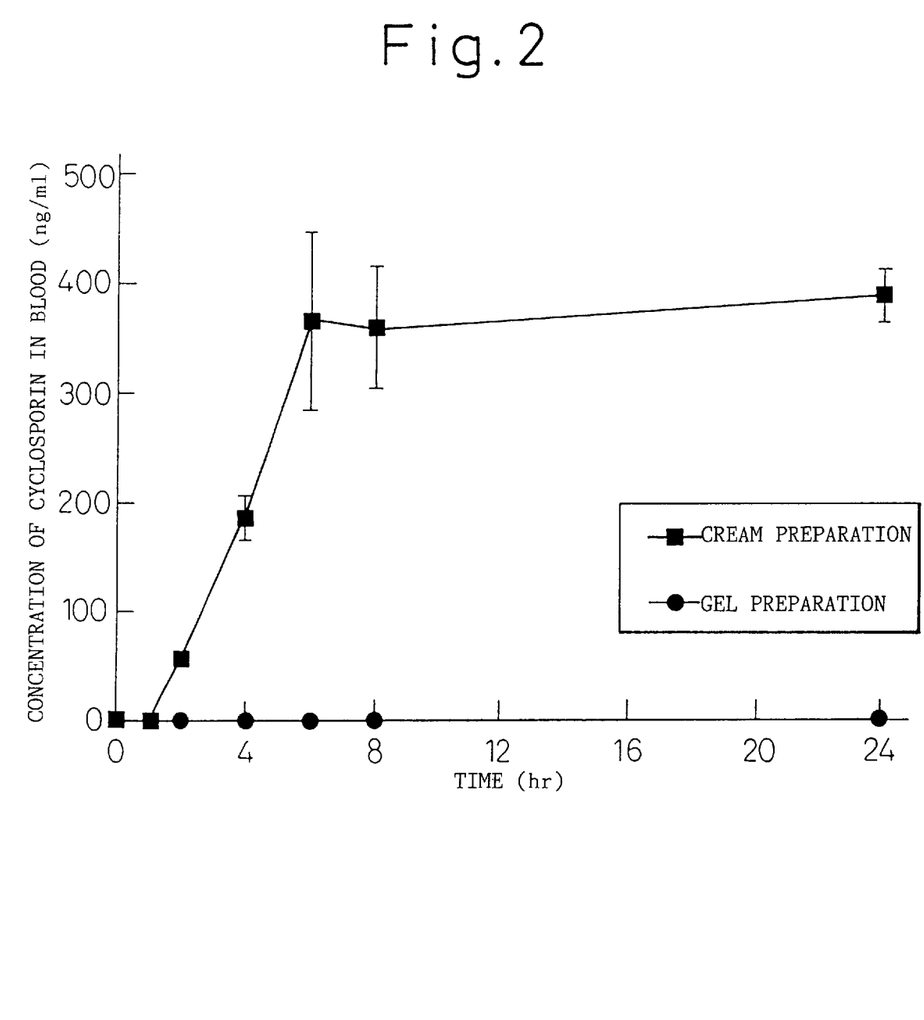
FIG. 2 is a graph showing transdermal absorption properties of the cream preparation of Example 3 and the gel preparation of Reference Example 1.

Approximately 1.2 g samples of the cream preparation of Example 3 and the gel preparation of Reference Example 1 were coated on the backs of groups of five C3H/Crj hairless mice (6 weeks old, body weight of approximately 25 g), then gauze was covered over the locations and affixed with tape. Blood was taken from the posterior artery at each of the following times after application and the concentration of the drug in the blood was measured. The assay was performed by the radioimmunoassay method. The results are shown in FIG. 2.

Experiment 4 (Immunosuppressive Effect on Contact Hypersensitivity)

The inhibitory effect on contact hypersensitivity was evaluated by inducing sensitization in groups of five dinitrochlorbenzene (DNCB) sensitized guinea pigs (6 weeks old, body weight of approximately 350 g), then immediately applying once at the same location of application of the DNCB approximately 1.0 g of a total of four preparations, i.e., the cream preparation of Example 3, the gel preparation of Reference Example 1, and the preparations of Example 3 and Reference Example 1 without cyclosporin as placebos. The evaluation was performed in accordance with the following criteria.

(Criteria for Evaluation of Positive Reaction)
(Formation of Erythema and Scabs)

| | |
|---|---|
| Slight erythema observed | 1 |
| Clear erythema observed | 2 |
| Medium degree of erythema observed | 3 |
| Strong erythema and slight scabs observed | 4 |
| (Formation of Edema) | |
| Edema not observed at all | 0 |
| Slight edema observed | 1 |
| Medium degree of edema observed | 2 |
| Strong edema observed | 3 |

Figure 3:
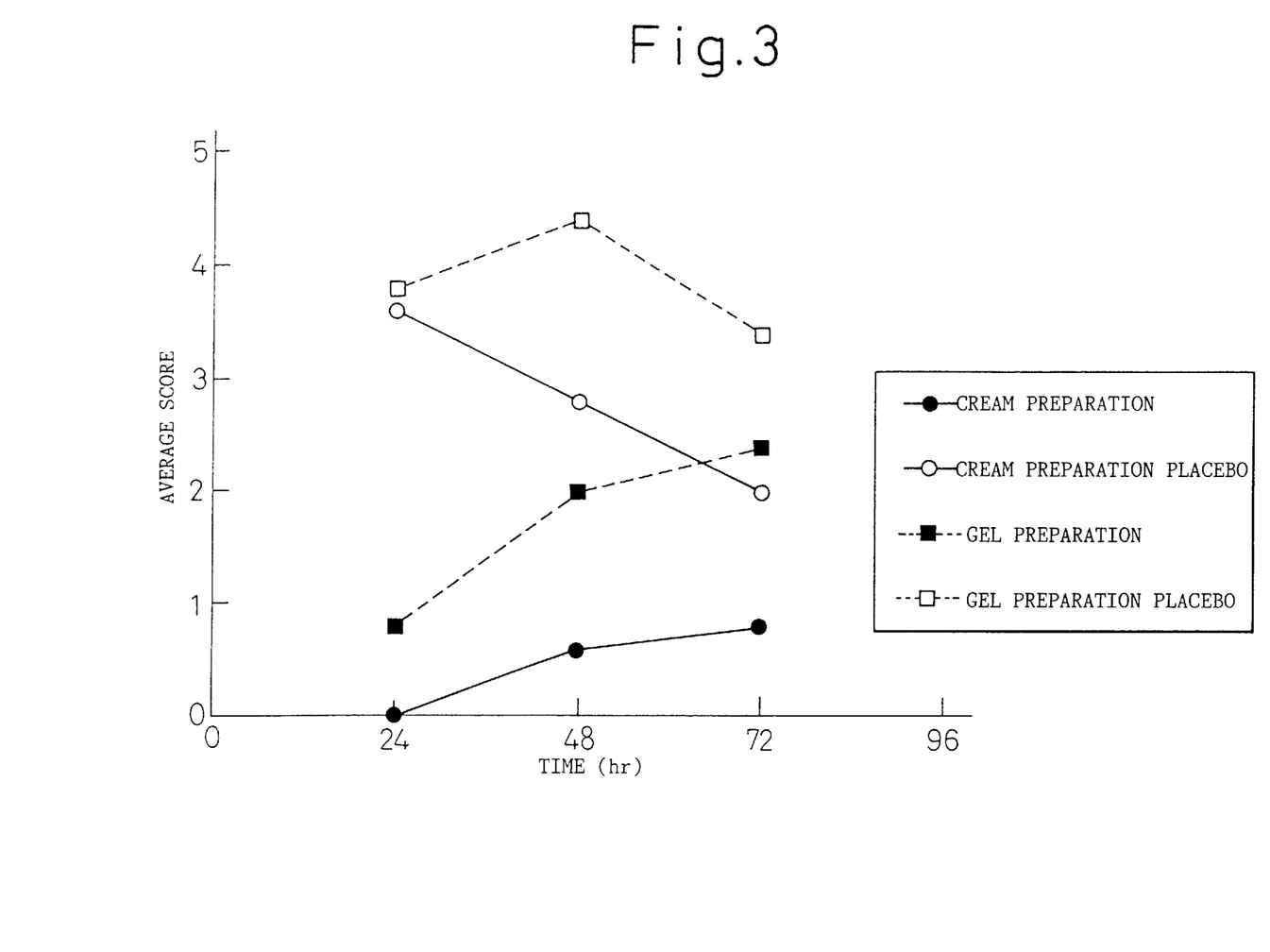
FIG. 3 is a graph showing the contact hypersensitivity inhibiting effect of the cream preparation of Example 3, the gel preparation of Reference Example 1, and control preparations not containing cyclosporin.

FIG. 3 shows the results of the examination of the rate of positive response using as a positive response the results of the mean score of the positive reaction or observation of clear erythema in Table 2.

TABLE 2

| | Rate of positive response | | |
|---|---|---|---|
| | After 24 hr | After 48 hr | After 72 hr |
| Cream preparation of Example 3 | 0/5 | 0/5 | 1/5 |
| Gel preparation of Reference Example 1 | 0/5 | 3/5 | 5/5 |

As is clear from the above results, the cream preparation of the present invention exhibits a strong inhibiting reaction on contact hypersensitivity compared with the gel preparation of the Reference Example. This is evidence of the superior transdermal absorption of the present invention.

INDUSTRIAL APPLICABILITY

The cyclosporin-containing oil-in-water emulsion composition according to the present invention has the superior properties that it enables a high concentration of cyclosporin to be mixed in, is superior in stability over time, exhibits an excellent transdermal absorption, and does not cause skin irritation.

We claim:

1. A cyclosporin-containing oil-in-water type emulsion composition comprising (a) cyclosporin, (b) a polyalkyl ester of polycarboxylic acid in the form of a liquid at ambient temperature, (c) at least one oil component selected from the group consisting of triglycerides, synthetic ester oils, squalene, liquid paraffins and silicone oils having an I.O.B. of 0 to 0.25 in the form of a liquid at ambient temperature, (d) a surfactant and (e) crotamiton.

2. An emulsion composition as claimed in claim 1, wherein the content of the cyclosporin is 0.1 to 10% by weight, based on the total weight of the emulsion composition.

3. An emulsion composition as claimed in claim 1, wherein the content of the polyalkyl ester of polycarboxylic acid is 2 to 50% by weight, based on the total weight of the emulsion composition.

4. An emulsion composition as claimed in claim 1, wherein the content of the oil component is 1/50 of the total weight of the cyclosporin and the polyalkyl ester of polycarboxylic acid.

5. An emulsion composition as claimed in claim 1, wherein the content of the surfactant is 0.5 to 15% by weight, based on the total weight of the emulsion composition.

6. An emulsion composition as claimed in claim 1, wherein the polyalkyl ester of polycarboxylic acid is selected from the group consisting of dibutyl phthalate, diethyl phthalate, dibutyl sebacate, diethyl sebacate, diisopropyl azelate, diisopropyl adipate, dibutyl adipate, and diisobutyl adipate.

7. An emulsion composition as claimed in claim 1, wherein the oil component having an I.O. B. of 0 to 0.25 in the form of a liquid at ambient temperature is selected from the group consisting of olive oil, soybean oil, oleyl oleate, diisopropyl myristate, cetyl myristate, squalane, liquid paraffin, and silicone oil.

* * * * *

UNITED STATES PATENT AND TRADEMARK OFFICE
CERTIFICATE OF CORRECTION

PATENT NO. : 5,891,846

DATED : April 6, 1999

INVENTOR(S) : Masami Ishida, et al.

It is certified that error appears in the above-indentified patent and that said Letters Patent is hereby corrected as shown below:

| | |
|---|---|
| Title Page [56], Other Publications, Line 8 | Delete "Sakaki" and substitute --Sazaki-- |
| Col. 12, Line 19 | Delete "the content of the oil component is 1/50 of the total weight of cyclosporin and the polyalkyl ester of polycarboxylic acid" and substitute --the ratio of the weight of the oil component to the total weight of the cyclosporin plus the polyalkyl ester of polycarboxylic acid ranges from 1:50 to 1:1 -- |

Signed and Sealed this

Twenty-third Day of November, 1999

Attest:

Q. TODD DICKINSON

*Attesting Officer*                *Acting Commissioner of Patents and Trademarks*